US 8,036,742 B2

(12) United States Patent
Sullivan et al.

(10) Patent No.: US 8,036,742 B2
(45) Date of Patent: Oct. 11, 2011

(54) APPARATUS AND METHODS FOR FIBRILLATION AND DEFIBRILLATION

(75) Inventors: Joseph L. Sullivan, Kirkland, WA (US);
Fred W. Chapman, Renton, WA (US);
Robert G. Walker, Bothell, WA (US)

(73) Assignee: Physio-Control, Inc., Redmond, WA (US)

( * ) Notice: Subject to any disclaimer, the term of this patent is extended or adjusted under 35 U.S.C. 154(b) by 1160 days.

(21) Appl. No.: 10/357,267

(22) Filed: Jan. 31, 2003

(65) Prior Publication Data

US 2004/0172068 A1 Sep. 2, 2004

(51) Int. Cl.
*A61N 1/39* (2006.01)
(52) U.S. Cl. .......................... 607/5; 607/2; 607/4; 607/9
(58) Field of Classification Search ................ 607/5, 4, 607/2, 9
See application file for complete search history.

(56) References Cited

U.S. PATENT DOCUMENTS

| | | | | |
|---|---|---|---|---|
| 3,527,229 A * | 9/1970 | Kempen | ............................. | 607/5 |
| 4,198,963 A * | 4/1980 | Barkalow et al. | ............. | 601/106 |
| 5,184,616 A * | 2/1993 | Weiss | ............................... | 607/4 |
| 5,346,506 A * | 9/1994 | Mower et al. | ...................... | 607/7 |
| 5,649,971 A * | 7/1997 | Fain et al. | ........................ | 607/72 |
| 5,653,740 A | 8/1997 | Degroot et al. | | |
| 6,148,233 A * | 11/2000 | Owen et al. | ........................ | 607/5 |
| 6,208,895 B1 * | 3/2001 | Sullivan et al. | .................... | 607/4 |
| 6,298,267 B1 | 10/2001 | Rosborough et al. | | |
| 6,356,785 B1 * | 3/2002 | Snyder et al. | ....................... | 607/5 |
| 6,418,342 B1 * | 7/2002 | Owen et al. | ......................... | 607/5 |
| 6,438,419 B1 * | 8/2002 | Callaway et al. | .................. | 607/5 |
| 6,477,413 B1 | 11/2002 | Sullivan et al. | | |
| 6,487,448 B2 | 11/2002 | Sullivan et al. | | |
| 6,963,773 B2 * | 11/2005 | Waltman et al. | ................... | 607/5 |
| 6,965,796 B2 * | 11/2005 | Kelly | ................................ | 607/4 |
| 2001/0031991 A1 | 10/2001 | Russial | | |
| 2003/0130697 A1 * | 7/2003 | Halperin et al. | ................... | 607/2 |
| 2004/0106955 A1 * | 6/2004 | Swerdlow et al. | ................ | 607/7 |

OTHER PUBLICATIONS

"Scaling Exponent Predicts Defibrillation Success for Out-of-Hospital Ventricular Fibrillation Cardiac Arrest", Circulation—Callaway et al., 2001, http://circ.ahajournals.org/cgi/content/full/103/12/1656 (13 pages).
Charles T. Leng et al., "Electrical Induction of Ventricular Fibrillation for Resuscitation From Postcountershock Pulseless and Asystolic Caridiac Arrests," Circulation, 7 pages, Aug. 7, 2001.

* cited by examiner

*Primary Examiner* — Niketa Patel
*Assistant Examiner* — Rex R Holmes
(74) *Attorney, Agent, or Firm* — Shumaker & Sieffert, P.A.

(57) ABSTRACT

The invention is directed to techniques for attempting to restore a patient to a normal sinus rhythm. In a patient experiencing asystole or pulseless electrical activity, defibrillation therapy may be ineffective. The invention is directed to techniques for delivering one or more shocks to induce ventricular fibrillation in the patient, followed by one or more defibrillation shocks to restore normal sinus rhythm. A defibrillator may deliver the fibrillation and defibrillation therapies. The invention may also include techniques for estimating the probability that the patient will respond favorably to the defibrillation therapy, and delivering defibrillation therapy when the therapy has a good probability of success.

33 Claims, 6 Drawing Sheets

APPARATUS AND METHODS FOR FIBRILLATION AND DEFIBRILLATION

FIELD

The invention relates to medical devices and, more particularly, to medical devices that deliver electrical energy to a patient.

BACKGROUND

Asystole and pulseless electrical activity (PEA) are cardiac rhythms with a very poor prognosis. When a patient suffers from asystole, the heart of the patient fails to contract. No ventricular depolarization takes place in the heart, cardiac output stops, and the patient is near death. The failure of the heart to generate a ventricular depolarization may be due to a failure of the electrical system of the heart, or may be caused by factors other than the electrical system.

PEA is the term applied to a group of conditions in which there may be detectable cardiac electrical activity but no detectable pulse. Although electrical activity is present in PEA, cardiac contractions may be absent. As a result, the heart of a patient suffering from PEA may produce insufficient cardiac output.

Asystole and PEA are grave cardiac rhythms. A patient experiencing either rhythm will die unless the heart assumes a contractile rhythm that restarts circulation. Unfortunately, asystole and PEA are typically not responsive to a defibrillation shock. Even if treated with medication and cardiopulmonary resuscitation (CPR), the odds of survival for the patient are low.

SUMMARY

In general, the invention is directed to techniques for attempting to restore a patient to a normal sinus rhythm. The techniques may include delivery of one or more shocks to induce ventricular fibrillation in a patient experiencing asystole or PEA. After ventricular fibrillation has been induced, the techniques may include delivery of one or more defibrillation shocks to restore normal sinus rhythm. A single medical device such as a defibrillator may deliver the defibrillation therapy and the fibrillation therapy as well.

The invention may further be directed to the timing of fibrillation and defibrillation therapies. Following induction of ventricular fibrillation, an operator such as an emergency medical technician (EMT) may perform CPR on the patient before defibrillation therapy is attempted. CPR may improve the probability that the patient will respond favorably to the defibrillation therapy. Analysis of the electrocardiogram (ECG) of the patient while the patient experiences ventricular fibrillation may indicate the probability of successful defibrillation therapy. One such analysis is the computation of a scaling exponent, which reflects a morphological analysis of a ventricular fibrillation waveform. The scaling exponent indicates the likely outcome of defibrillation therapy. The invention encompasses embodiments in which a medical device delivers fibrillation therapy to a patient, monitors the scaling exponent to determine when delivery of defibrillation therapy has a good probability of success, then delivers defibrillation therapy.

In one embodiment, the invention is directed to a device comprising a monitoring module to monitor electrical activity of a heart of a patient, an electrical source to generate a first electrical shock to induce fibrillation of the heart and a second electrical shock to defibrillate the heart, and at least two electrodes to deliver the first and second shocks to the heart.

In another embodiment, the invention is directed to a method comprising detecting asystole or PEA in a heart of a patient, delivering a first electrical shock to induce fibrillation of the heart and delivering a second electrical shock to defibrillate the heart. The method may further include prompting an operator to perform CPR on the patient following delivery of the first electrical shock, and prompting the operator to discontinue performing CPR on the patient prior to delivery of the second electrical shock. The method may also include estimating the effectiveness of the second electrical shock prior to delivery of the second electrical shock, such as by computing a scaling exponent.

In a further embodiment, the invention is directed to a method comprising delivering a defibrillation shock to a heart in fibrillation and delivering a fibrillation shock to the heart when one of asystole and pulseless electrical activity follows the defibrillation shock. This method may be useful when, for example, defibrillation therapy causes the patient to experience asystole or PEA, rather than normal sinus rhythm.

In another embodiment, the invention presents a method comprising detecting asystole in a heart of a patient, delivering fibrillation therapy comprising at least one electrical shock to induce fibrillation of the heart, and discontinuing a therapy upon failure of the fibrillation therapy to induce fibrillation. The method may also include notifying an operator that the fibrillation therapy has failed to induce fibrillation. This method may be useful in situations in which an operator needs to make a decision about what rescue efforts, if any, ought to be made to save the patient. In general, a patient experiencing asystole may be more likely to respond to an effort to induce fibrillation than other resuscitative efforts. It may be of importance to the operator to know that, should the patient fail to respond to fibrillation therapy, the chances of restoring a normal sinus rhythm may be extremely remote.

The invention further includes computer-readable media comprising instructions for causing a programmable processor to carry out the methods described above.

The invention may offer one or more advantages. For example, the availability of both fibrillation and defibrillation therapies in a single device may permit emergency treatment of patients exhibiting asystole or PEA. In particular, a single device may be used to deliver monophasic defibrillation therapy, multiphasic defibrillation therapy and fibrillation therapy. The device may include circuitry that supports each type of therapy, thereby saving space, weight and expense.

An increased chance of survival for some patients may be a further advantage of the invention. A patient exhibiting asystole or PEA has a low chance of survival, but the techniques of the invention may improve the patient's chance of survival. Further, some embodiments of the invention include techniques for controlling the timing of fibrillation and defibrillation therapies, possibly further enhancing the chance of survival.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
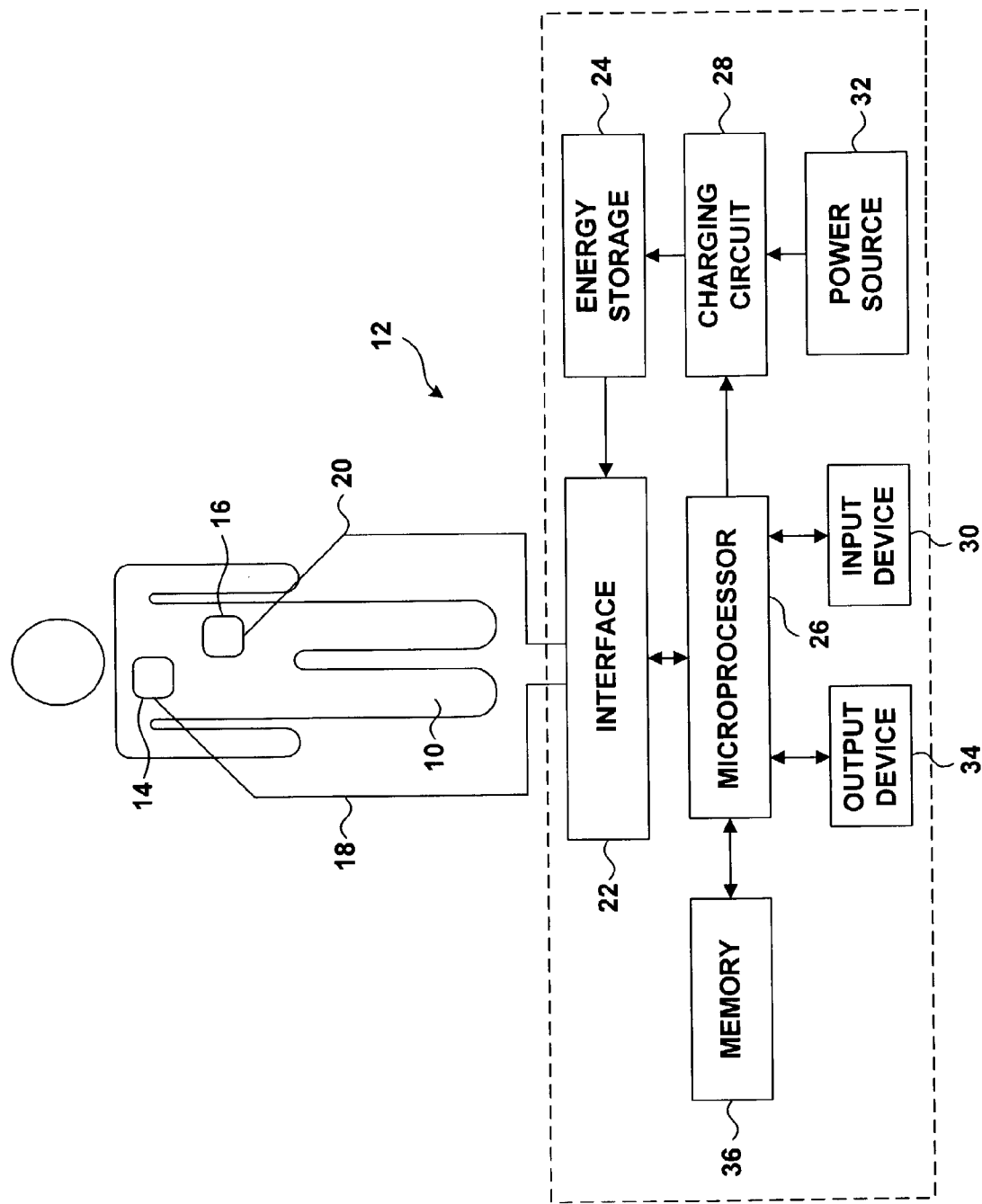
FIG. 1 is a schematic diagram of a defibrillator that may be used to practice the techniques of the invention.

FIG. 1 is a block diagram showing a patient 10 coupled to an external defibrillator 12. External defibrillator 12 is one example of a medical device that may be used to practice the invention. Defibrillator 12 may be, for example, an automated external defibrillator (AED), but the techniques of the invention may be practiced with a manual defibrillator as well.

Defibrillator 12 is capable of administering both fibrillation and defibrillation therapy to patient 10 via electrodes 14 and 16, which may be hand-held electrode paddles or adhesive electrode pads placed externally on the skin of patient 10. The body of patient 10 provides an electrical path between electrodes 14 and 16.

Electrodes 14 and 16 are coupled to defibrillator 12 via conductors 18 and 20 and interface 22. In a typical application, interface 22 includes a receptacle, and connectors 18, 20 plug into the receptacle. Electrical impulses or signals may be sensed by defibrillator 12 via electrodes 14 and 16 and interface 22. Electrical impulses or signals may also be delivered from defibrillator 12 to patient 10 via electrodes 14 and 16 and interface 22.

Energy storage device 24 stores energy for fibrillation and defibrillation therapy in energy storage components, such one or more charged capacitors. Interface 22 includes one or more switches (not shown in FIG. 1) that, when activated, deliver energy stored in an energy storage device 24 to electrodes 14 and 16. Energy storage device 24 and interface 22 cooperate to function as an electrical source that generates electrical shocks that deliver energy to patient 10. The shocks may induce fibrillation of the heart of patient 10, or may defibrillate the heart. Although the shocks may be described in terms of voltage or current, for convenience delivery of energy will be described in terms of delivery of electric current.

Interface 22, in addition to controlling when current may flow to patient 10, may also regulate the direction of current flow, under the control of a microprocessor 26. When defibrillator 12 delivers a monophasic defibrillation shock, microprocessor 26 controls interface 22 to route current through the body of patient 10 from electrode 14 to electrode 16. When defibrillator 12 delivers a multiphasic defibrillation shock, the direction of current flow changes one or more times. In a biphasic defibrillation shock, for example, microprocessor 26 controls interface 22 to route current through the body of patient 10 from electrode 14 to electrode 16, then in the opposite direction, from electrode 16 to electrode 14.

Microprocessor 26 may serve as a monitoring module that monitors the electrical activity in the heart of patient 10. For example, microprocessor 26 may analyze electrical impulses or signals sensed via electrodes 14 and 16. The electrical signals may include an electrocardiogram (ECG), which reflects the electrical activity of the heart. Microprocessor 26 may, for example, apply algorithms to determine whether the ECG of patient 10 exhibits significant electrical activity of the heart, and whether the electrical activity is indicative of a normal heart rhythm or an arrhythmia. Microprocessor 26 may further estimate the likely effectiveness of therapy for an arrhythmia. For example, microprocessor 26 may compute a scaling exponent of a signal indicative of ventricular fibrillation, and estimate the effectiveness of defibrillation therapy as a function of the computed scaling exponent. The utility of the scaling exponent will be discussed in more detail below.

When delivering fibrillation therapy, microprocessor 26 controls interface 22 to deliver current to induce fibrillation. Current to induce fibrillation may comprise a sequence of pulses in alternating directions, as described below. When fibrillation therapy is called for, interface 22 operates as a fibrillation circuit, under the control of microprocessor 26. Fibrillation therapy may be appropriate, for example, when a patient is experiencing asystole or PEA. Fibrillation therapy will be discussed in more detail below.

1 Before energy may be delivered to patient 10 as part of fibrillation or defibrillation therapy, charging circuit 28 stores energy in energy storage device 24. Microprocessor 26 directs charging circuit 28 to charge energy storage device 24 to a high voltage level. Microprocessor 26 may automatically direct charging circuit 28 to begin charging, or microprocessor 26 may direct charging circuit 28 to begin charging upon the instruction of an operator such as an EMT. An operator may instruct microprocessor 26 with an input device 30, such as a button, a keyboard, a touch screen, a voice recognition module or a pointing tool.

Charging circuit 28 comprises, for example, a flyback charger that transfers energy from a power source 32 to energy storage device 24. Power source 32 may include an adapter to an exterior power source such as an electrical outlet, making defibrillator 12 "line-powered." In many situations, however, patient 10 may be far from an electrical outlet. Accordingly, power source 32 may comprise a battery, making defibrillator 12 portable and useful in a wider variety of emergency situations. In addition to supplying energy to charging circuit 28 and energy storage device 24, power source 30 may also supply power to components, such as microprocessor 26, via a power supply circuit (not shown in FIG. 1).

Charging circuit 28 transfers energy from power source 32 to energy storage device 24 until the energy stored in energy storage device 24 reaches a desired level. At that point, defibrillator 12 is ready to deliver the fibrillation or defibrillation therapy. The therapy may be delivered automatically or manually.

When defibrillator 12 delivers fibrillation therapy, action by the operator may be indicated. In particular, defibrillator 12 may prompt the operator to perform CPR following delivery of the fibrillation therapy. Defibrillator 12 may prompt the operator using an output device 34, such as a display screen, an audible sound generator, a voice synthesizer, a printer or an indicator light. Defibrillator 12 may further use output device 34 to prompt the operator to deliver a defibrillating pulse following CPR, or to warn the operator to move clear of patient 10 when a fibrillating or defibrillating current is about to be delivered to patient 10.

In some embodiments of the invention, defibrillator 12 may include or control a chest compressor. A chest compressor is a medical device that physically compresses the chest of patient 10 and that can perform CPR. In that embodiment, defibrillator 12 may, instead of prompting the operator to perform CPR, direct the chest compressor to do so.

In some embodiments of the invention, an output device 34 such as a display screen may be used as a monitoring module that monitors the electrical activity in the heart of patient 10. The screen may display an ECG waveform, for example, from which a trained operator may evaluate the electrical activity of the heart. In these embodiments, output device 34 may supplement or supplant the monitoring functions of microprocessor 26.

Microprocessor 26 may retrieve instructions pertaining to fibrillation and defibrillation therapies from memory 36. Memory 36 may include volatile storage, such as random access memory, and/or non-volatile storage, such as Flash memory or a hard disk. Memory 36 stores instructions that direct the operation of microprocessor 26. In addition, memory 36 stores information about patient 10 and defibrillator 12. For example, memory 36 may store data about electrical signals sensed by defibrillator 12 and the response of patient 10 to therapy.

Figure 2:
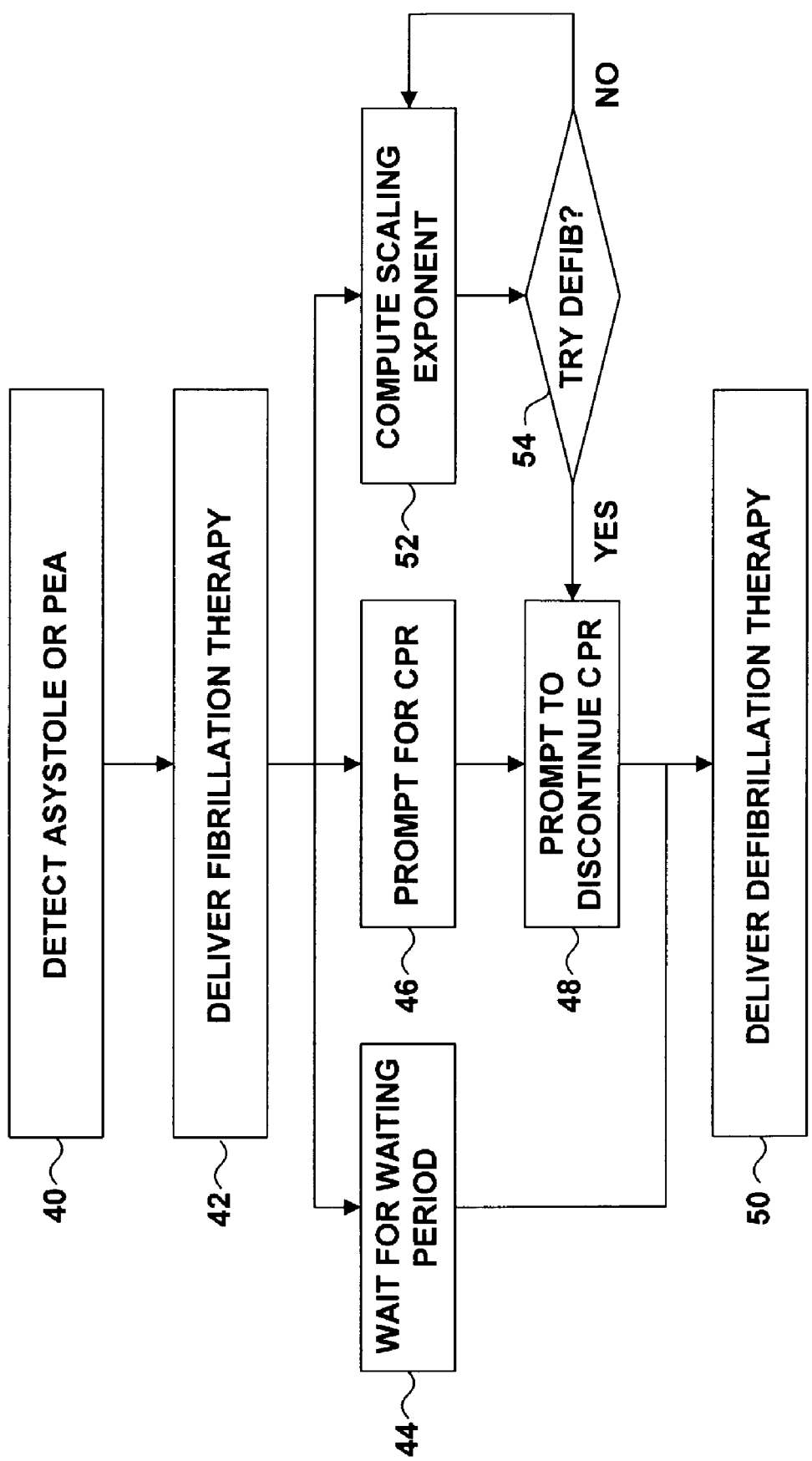
FIG. 2 is a flow diagram illustrating a technique for applying fibrillation and defibrillation therapies.

FIG. 2 is a flow diagram illustrating a treatment involving fibrillation and defibrillation. Defibrillator 12 may detect asystole or PEA (40) using any of several techniques. The invention includes detection based upon a diagnosis from an operator. In an emergency, an operator such as an emergency medical technician may diagnose the asystole or PEA. Defibrillator 12 may receive notification from the operator via input device 30 that the patient is experiencing asystole or PEA. Defibrillator 12 also may use automatic detection techniques based, for example, upon detected electrical activity or inactivity or measurements of the impedance of the patient.

In some circumstances, defibrillator 12 may detect asystole or PEA by detection of a change in the electrical activity of patient 10, or detection of a lack of electrical activity. Such circumstances may exist when, for example, a patient experiencing ventricular fibrillation receives a defibrillation shock, and responds by experiencing asystole or PEA.

When asystole or PEA has been detected, defibrillator 12 may begin fibrillation therapy (42). Fibrillation therapy may comprise delivering a time-varying current to the heart of patient 10, as described below, and then evaluating the ECG to determine whether patient 10 is indeed experiencing ventricular fibrillation. If one delivery of time-varying current fails to induce fibrillation, another time varying current, typically of a greater magnitude, may be delivered. Several attempts to induce fibrillation may be needed.

When patient 10 begins to experience fibrillation, a waiting period (44) begins, during which defibrillator 12 delivers no therapy. During the waiting period (44), defibrillator 12 may prompt the operator to perform CPR (46), and microprocessor 26 may direct charging circuit 28 to store energy in energy storage device 24 so that defibrillator 12 will be able to deliver defibrillation therapy. In embodiments of the invention in which defibrillator 12 includes or controls a chest compressor, defibrillator 12 may perform CPR rather than prompt an operator to do so. At the conclusion of the waiting period (44), defibrillator 12 may prompt the operator to discontinue CPR (48) or, when CPR is performed by a chest compressor, defibrillator 12 may direct the device to discontinue CPR. Defibrillator 12 may deliver defibrillation therapy (50).

The goal of defibrillation therapy is to depolarize the heart with electrical current and cause the heart to reestablish a normal sinus rhythm. A patient experiencing ventricular fibrillation may be more likely to respond to resuscitative efforts than a patient experiencing asystole or PEA. For a patient having asystole or PEA, therefore, it may be possible to restore a sinus rhythm by inducing ventricular fibrillation first, followed by defibrillation.

There is no guarantee that fibrillation therapy (42), followed by defibrillation therapy (50), will restore a normal sinus rhythm. Asystole and PEA, however, are very grave conditions. In asystole and PEA, the heart of the patient exhibits an absence of mechanical activity, and unless the pumping action of the heart is restored, the patient will die.

Fibrillation therapy may cause the heart to reacquire some mechanical activity. When the heart is undergoing ventricular fibrillation, the heart contracts in an uncoordinated fashion in response to erratic electrical impulses. This mechanical activity is ineffective in pumping blood, so the patient should ordinarily be given CPR following administration of fibrillation therapy.

In addition to assisting the pumping of blood, CPR may also increase the chances of a successful defibrillation following ventricular fibrillation. Clinical data have shown that it may be possible to assess the probability of a successful defibrillation by morphological analysis of the ECG waveform exhibited by a patient in ventricular fibrillation. One way to quantify the probability of a successful defibrillation is to compute a scaling exponent. In general, a "scaling exponent" is a quantity that reflects a morphological analysis of a ventricular fibrillation waveform. In particular, a scaling exponent is an estimate of the fractal self-similarity dimension that characterizes the roughness or smoothness of the ventricular fibrillation waveform, which in turn indicates the likely outcome of defibrillation therapy.

Defibrillator 12 may estimate the effectiveness of defibrillation therapy as a function of the scaling exponent. The scaling exponent may reflect the chances that defibrillation will result in restoration of a normal rhythm, which is a desirable outcome. The scaling exponent may also reflect the chances that defibrillation will result in an undesirable outcome, such as asystole, PEA, or a return to ventricular fibrillation. Clinical data have further shown that a scaling exponent may "improve" with administration of CPR. That is, a scaling exponent may be indicative of an undesirable outcome, but administration of CPR may cause the scaling exponent to change so as to indicate an improved probability of a desirable outcome. When the scaling exponent reflects an acceptable probability of a desirable outcome, defibrillator 12 may discontinue CPR (48) and may attempt defibrillation (50).

While patient 10 experiences ventricular fibrillation, microprocessor 26 may analyze the ECG detected via electrodes 14 and 16, and compute a scaling exponent (52). During CPR, several scaling exponents may be computed. When a scaling exponent indicates that defibrillation therapy may be beneficial (54), defibrillator 12 may prompt to discontinue CPR (48), end the waiting period, and deliver defibrillation therapy (50).

The scaling exponent may indicate that defibrillation therapy may be beneficial when, for example, the scaling exponent surpasses a predetermined threshold value. Defibrillator 12 may deliver defibrillation therapy when, for example, the scaling exponent falls below a predetermined value. The scaling exponent may also indicate that defibrillation therapy may be beneficial when the value of the scaling exponent "levels off," suggesting that further improvement in the ventricular fibrillation waveform is unlikely. In such circumstances, defibrillation therapy may have a better probability of success than continued CPR.

It is possible that patient 10 may respond to defibrillation therapy by going into asystole or PEA. In that case, fibrillation therapy may be delivered again (42) and the techniques described above may be repeated. It is also possible that patient 10 may remain in ventricular fibrillation. In that case, CPR may begin again (46) and new scaling exponents may be computed (52), followed by another attempt at defibrillation (50). Another possibility is that patient 10 may return to a normal sinus rhythm.

Fibrillation therapy involves delivery of a time-varying current to the heart of patient 10. Experience has demonstrated that current delivered at about 60 cycles per second may induce fibrillation. By coincidence, 60 cycles per second is the standard alternating current frequency in the United States. Accordingly, it is possible for a line-powered defibrillator to deliver fibrillation therapy by stepping down the line voltage with a transformer and delivering the alternating current to patient 10. As noted above, however, patient 10 may be far from an electrical outlet. Accordingly, defibrillator 12 may include circuitry to deliver current varying at 60 cycles per second.

Figure 3:
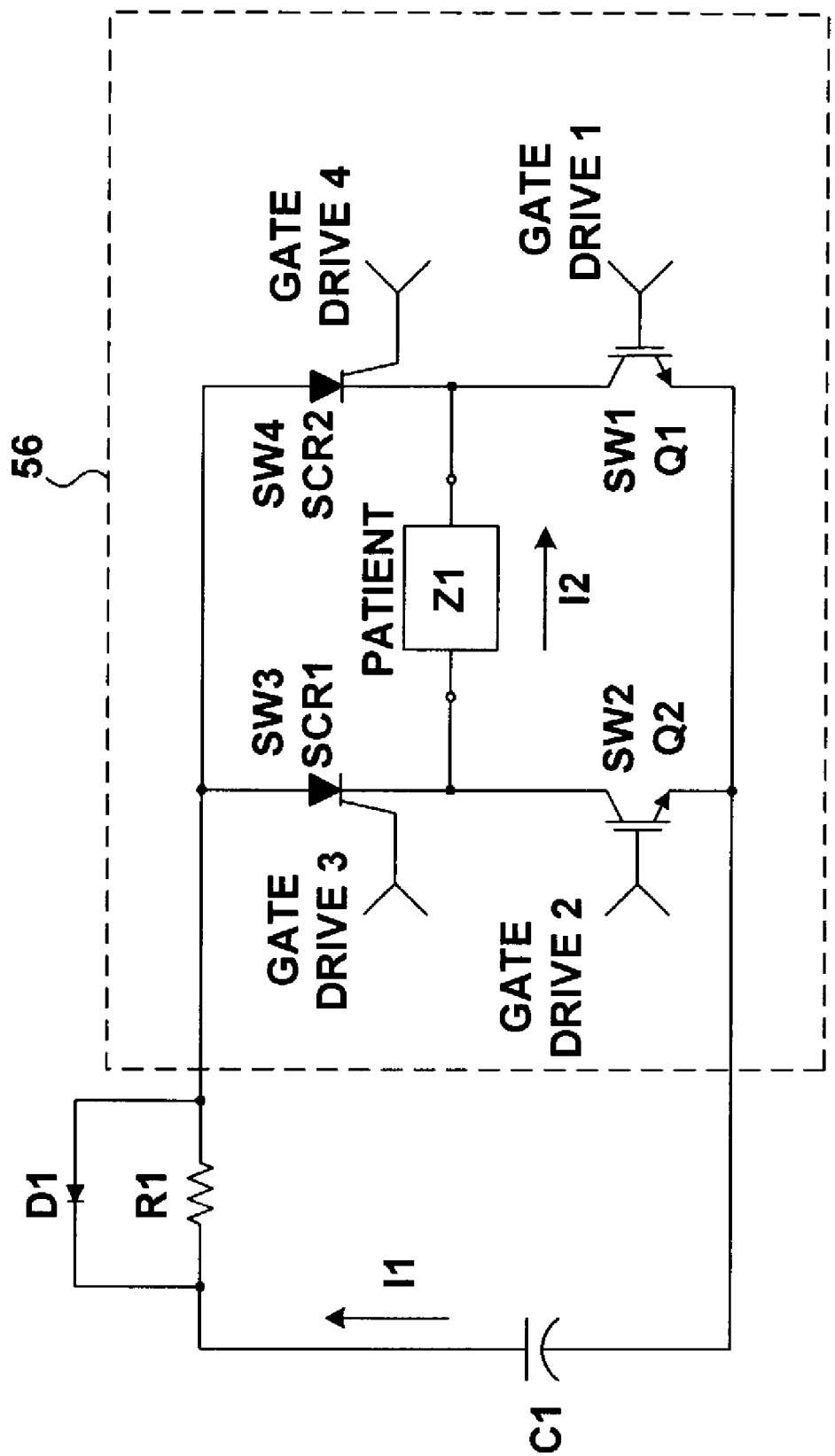
FIG. 3 is a diagram of a circuit model that may deliver time-varying fibrillation current, as well as monophasic and multiphasic defibrillation currents.

FIG. 3 is a circuit diagram of a model that may deliver time-varying fibrillation current. In FIG. 3, energy storage device 24 is modeled as high-voltage capacitor C1. Patient 10 is modeled as an impedance element Z1. Patient impedance Z1 may be expected to fall between 25 and 200 ohms, with a typical patient impedance being about 75 to 80 ohms. Patient impedance Z1 comprises a resistive component and a reactive component.

Capacitor C1 supplies current in the direction indicated by arrow I1 to an H-bridge circuit 56 comprising switched solid-state circuit elements. As shown in FIG. 3, switched circuit elements may include insulated gate bipolar transistors Q1 and Q2, which serve as switches 1 and 2 (SW1 and SW2) and silicon controlled rectifiers SCR1 and SCR2, which serve as switches 3 and 4 (SW3 and SW4).

Switches SW1, SW2, SW3 and SW4 are not limited to the components shown, however, and may include any combination of solid-state switches. For example, SW1, SW2, SW3 and SW4 may be embodied as field-effect transistors. In addition, switches SW1, SW2, SW3 and SW4 may employ more components than shown. SW1, for example, may include two or more insulated gate bipolar transistors to divide the voltage across SW1.

Although FIG. 3 includes protection circuitry represented by resistor R1 and diode D1, the circuit may also include additional switch protection circuitry to prevent spurious voltage spikes from damaging the switches. A resistor such as R1 may also be selected or controlled to regulate the time constant of the circuit, and thereby regulate how rapidity capacitor C1 delivers stored energy to patient Z1.

When switches SW1 and SW3 are closed and switches SW2 and SW4 are open, current from capacitor C1 flows through patient Z1 in the direction indicated by arrow 12. When switches SW1 and SW3 are open and switches SW2 and SW4 are closed, current from capacitor C1 flows through patient Z1 in the direction opposite that indicated by arrow 12. A control signal regulates whether a switch is open or closed. Gate drive 1 is the control signal that regulates SW1, gate drive 2 is the control signal that regulates SW2, and so on. Microprocessor 26 (not shown in FIG. 3) controls the gate drive signals, typically by controlling driving circuits (not shown in FIG. 3). In this way, microprocessor 26 controls whether current flows through the patient as well as the direction of current flow through the patient.

By controlling the timing and direction of current flow through the patient, microprocessor 26 controls delivery of a time-varying fibrillation current to the patient. In addition, microprocessor 26 may control H-bridge circuit 56 to deliver a monophasic direct current pulse to defibrillate the patient. Microprocessor 26 may also control H-bridge circuit 56 to deliver multiphasic defibrillation pulses to the patient.

Figure 4:
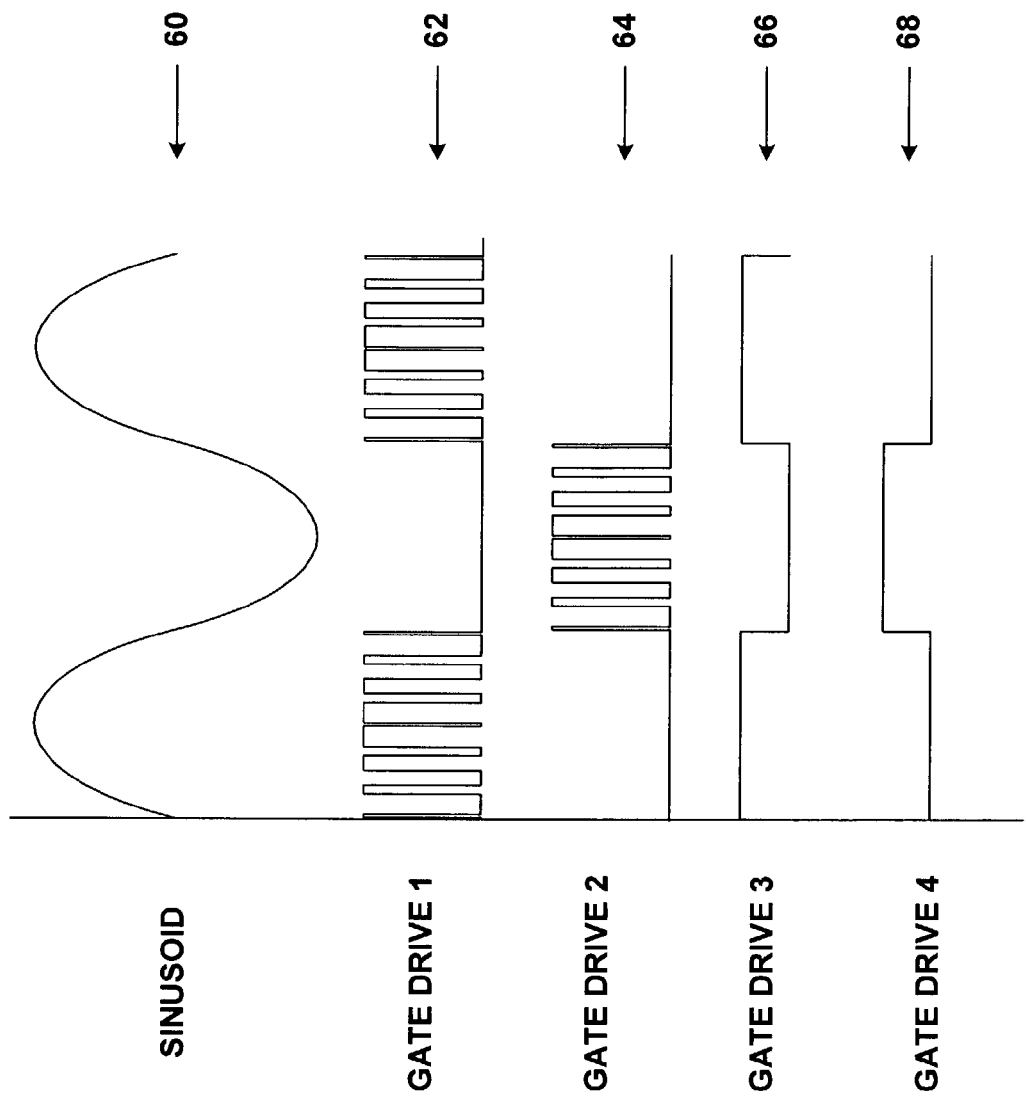
FIG. 4 depicts waveforms of time-varying fibrillation current that may be delivered to the patient via a circuit such as that modeled in FIG. 3.

FIG. 4 illustrates waveforms of time-varying fibrillation current that may be delivered to the patient via a circuit such as that depicted in FIG. 3. Sinusoidal waveform 60 represents a 60 Hz waveform that has been experimentally established to induce fibrillation. In line-powered embodiments of the invention, sinusoidal waveform 60 may be delivered to the patient by stepping down the line voltage with a transformer. In battery-powered embodiments of the invention, however, it may not be efficient to deliver a 60 Hz sinusoidal waveform.

Defibrillator 12 may, however, deliver a substantial equivalent of a 60 Hz sinusoidal waveform by delivering a sequence of pulses as shown in FIG. 4. Gate drive 1 control signal 62 and gate drive 2 control signal 64 comprise pulse-width modulated signals that open and close SW1 and SW2. Gate drive 3 control signal 66 and gate drive 4 control signal 68 need not be modulated, but may simply turn on and off to direct the flow of current in a desired direction.

Because the patient impedance Z1 includes a reactive component, the body of the patient may behave as a low pass filter that smoothes the pulses, producing an approximation of a 60 Hz sine wave. Control signals 62 and 64 may control the amplitude and width of the pulses to generate a close approximation of a 60 Hz sine wave of a desired current magnitude. As shown in FIG. 4, for example, control signals 62 and 64 may include pulses that increase in pulse width and decrease in pulse width. Because the sequence of pulses in the body of the patient are approximately similar to a 60 Hz sine wave 60, the sequence of pulses may have the same effect as a 60 Hz sine wave, and may induce ventricular fibrillation.

A 60 Hz sine wave may also be generated from a direct current electrical source using wave-shaping circuits or inverters, but the use of pulse-width modulated signals may have advantages over those techniques. First, pulse-width modulated signals may be generated by existing defibrillator circuitry for delivery of monophasic and multiphasic pulses. Use of existing circuitry to generate an approximation of a sine wave may result in a saving of space, weight and expense.

Second, the time constant of the system may affect how rapidly energy may be delivered to patient 10. Defibrillator 12 may be configured to deliver high current dosages in a short period of time in accordance with defibrillation therapy. Even though defibrillator 12 may be configured to deliver high current dosages in a short period of time, pulse-width modulated signals may be used to deliver the current in smaller doses over a longer time, in accordance with fibrillation therapy. The current needed for fibrillation may be substantially less than the current needed for defibrillation. Fibrillation therapy may employ currents of about 1 to 4 amperes, for example, while defibrillation therapy may employ currents in the range of about 20 to 40 amperes. Pulse-width modulated signals may therefore result in an efficient use of the energy stored in energy storage device 24.

Third, pulse-width modulated signals may represent an efficient technique for managing the magnitude of current delivered to patient 10 during fibrillation therapy. As mentioned above, patient 10 may initially fail to respond to fibrillation therapy, and fibrillation therapy may be repeated at a higher current magnitude. Should patient 10 fail to respond to fibrillation therapy at 1 ampere, for example, a second fibrillation therapy may be delivered at 2 amperes. If needed, a third fibrillation therapy may be delivered at 3 amperes, and so on. By changing the timings and widths of the pulses, defibrillator 12 may deliver fibrillation therapy at different current magnitudes.

Fourth, pulse-width modulated signals may be used to deliver fibrillation therapy at a variety of waveforms and frequencies. For example, the pulses may approximate another waveform that may induce fibrillation, such as a square wave or triangular wave, and may set the effective frequency of the waveform to be greater than or less than 60

Hz. In the event a patient does not respond to an approximation of a 60 Hz sine wave, fibrillation therapy may be attempted with another waveform or another frequency or both.

The invention is not limited to fibrillation therapy having any particular frequency. Nor is the invention limited to fibrillation therapy having any particular strength or duration. The strength and duration of fibrillation therapy may be a function of the capabilities of energy storage device 24 and power supply 32. As noted above, the magnitude of the current needed for fibrillation may be substantially less than the magnitude of the current needed for defibrillation. Fibrillation therapy may have a duration that exceeds defibrillation therapy, but it is believed that fibrillation may be induced with alternating currents of shorter durations than may be used in hospital settings. Fibrillation therapy delivered over approximately one-half a second, for example, may be sufficient to induce ventricular fibrillation.

Figure 5:
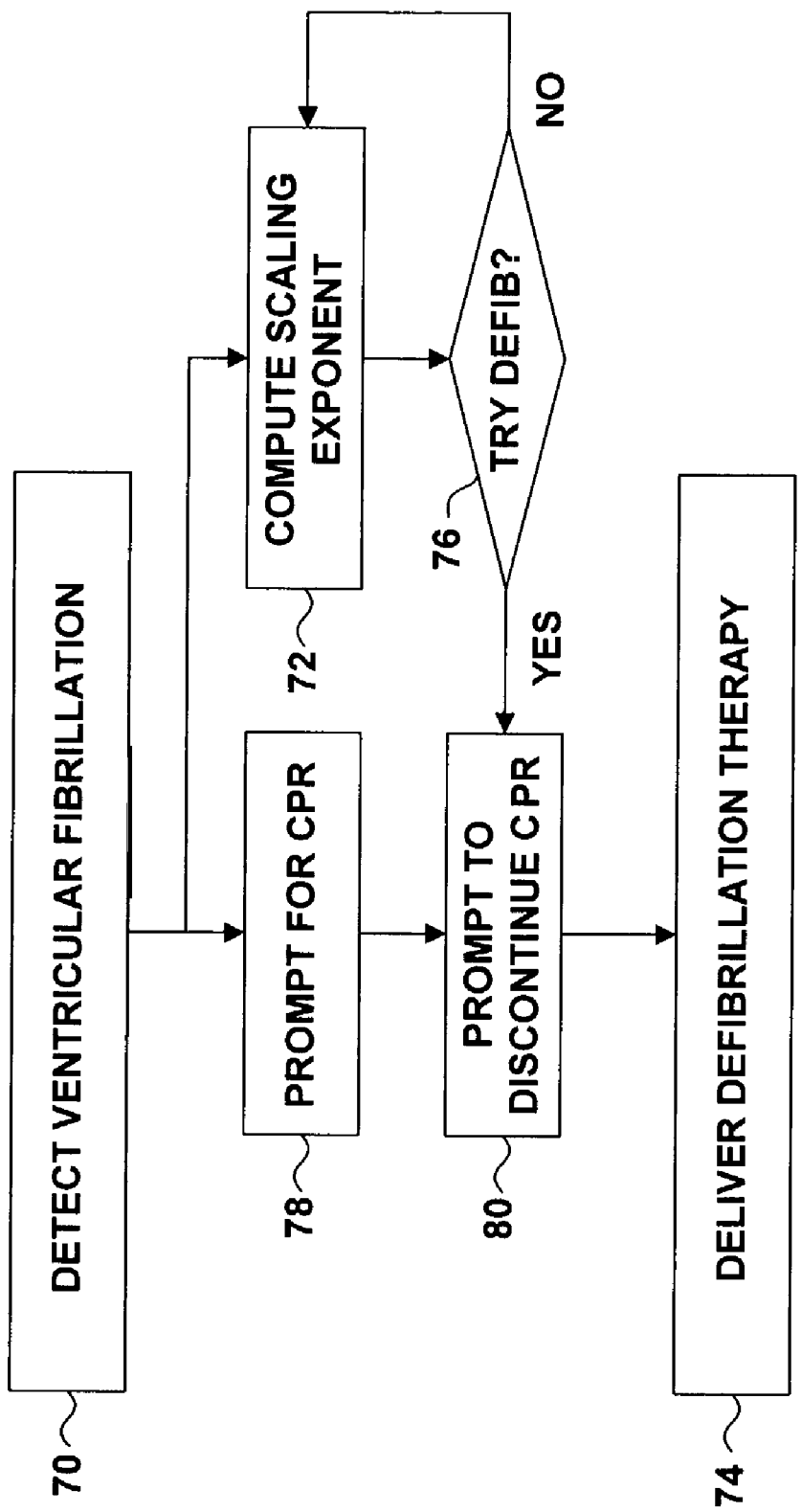
FIG. 5 is a flow diagram illustrating a technique for applying defibrillation therapy to a patient experiencing ventricular fibrillation.

FIG. 5 is a flow diagram illustrating techniques that may be employed in place of or in addition to the techniques shown in FIG. 2. In FIG. 5, defibrillator 12 detects ventricular fibrillation (70) rather than asystole or PEA. In some cases, treatment of ventricular fibrillation with defibrillation therapy may cause patient 10 to experience asystole or PEA, rather than a normal sinus rhythm.

Accordingly, defibrillator 12 may compute a scaling exponent (72) before delivering defibrillation therapy (74), and may deliver defibrillation therapy (74) when the scaling exponent indicates that defibrillation therapy may be beneficial (76). Defibrillator 12 may also prompt the operator to deliver CPR (78) and to suspend CPR (80) before delivering defibrillation therapy (74). In embodiments of the invention in which defibrillator 12 includes or controls a chest compressor, defibrillator 12 may control delivery and suspension of CPR before delivering defibrillation therapy (74).

Defibrillation therapy (74) may result in restoration of a normal sinus rhythm. Even when the scaling exponent indicates that defibrillation therapy may be beneficial, the scaling exponent reflects a probability of a desirable outcome, not a guarantee of a desirable outcome. In some cases, defibrillation therapy (74) may result in asystole or PEA. In such cases, defibrillator 12 may employ the techniques shown in FIG. 2 to recover from asystole or PEA.

Figure 6:
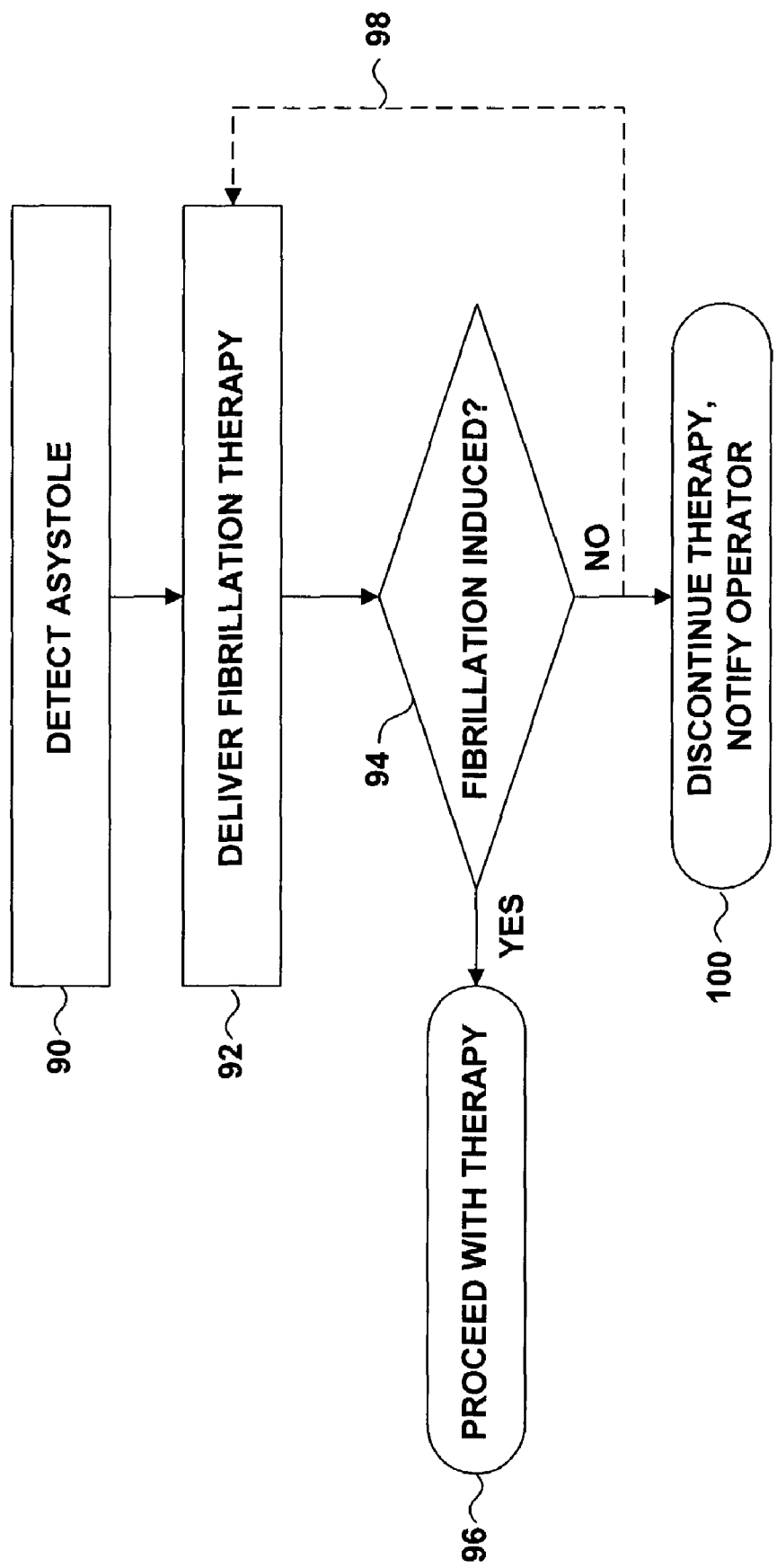
FIG. 6 is a flow diagram illustrating a technique for performing and discontinuing fibrillation therapy.

FIG. 6 is a flow diagram illustrating techniques that may be employed in place of or in addition to the techniques shown in FIG. 2. In FIG. 6, defibrillator 12 detects asystole (90). Defibrillator 12 may detect asystole by, for example, receiving notification from an operator via input device 30. Defibrillator 12 may also confirm the absence of electrical cardiac activity when defibrillator 12 fails to sense electrical impulses or signals from patient 10 via electrodes 14 and 16. When asystole has been detected, defibrillator 12 may begin fibrillation therapy (92), using techniques described above.

Fibrillation therapy may be successful (94), i.e., patient 10 may begin to experience fibrillation. In such a case, the therapy may proceed with therapy (96) as described above in connection with FIG. 2. It is also possible, however, that fibrillation therapy may be unsuccessful (94), i.e., the heart may fail to exhibit a response to the fibrillation therapy. Fibrillation therapy may thereafter be repeated (98) one or more times. If patient 10 fails to respond to fibrillation therapy, therapy may be discontinued, and defibrillator 12 may so notify the operator (100).

A patient may be more likely to respond to fibrillation therapy than to other to resuscitative efforts. When a patient fails to respond to fibrillation therapy, then the chances of restoring a normal sinus rhythm may be extremely remote. When fibrillation cannot be induced in the patient, further rescue efforts may be futile. The patient has very likely expired.

There may be many circumstances in which a choice must be made as to whether to continue rescue efforts or to terminate rescue efforts. For example, when a patient is found in an inaccessible location, and the patient is unconscious and without a heartbeat, it may be necessary to make a choice whether a risky and expensive rescue operation is warranted or not. Should repeated attempts to induce fibrillation fail, then it is likely that further rescue efforts would also be unsuccessful.

The techniques depicted in FIG. 6 may therefore present a diagnostic procedure that an operator may use to determine whether to pursue further care or whether to terminate care. When defibrillator 12 notifies the operator that patient 10 is not responsive to fibrillation therapy, the operator may use the information conveyed in the notification to make a decision. The operator may decide to direct defibrillator 12 to attempt fibrillation therapy anew (92), for example, or may decide to apply another therapy such as CPR, or may decide to discontinue all rescue efforts.

Although described in connection with a defibrillator, the techniques described in FIG. 6 may be practiced by medical devices that provide patient care in addition to fibrillation therapy. For example, a device may provide therapy such as cardiac pacing or chest compression. In the event that patient 10 fails to respond to fibrillation therapy, any or all of these therapies may be discontinued (100).

Some of the techniques described above may be embodied as a computer-readable medium comprising instructions for a processor such as microprocessor 26. A "computer-readable medium" includes but is not limited to read-only memory, Flash memory and a magnetic or optical storage medium. The medium may comprise instructions for causing a programmable processor to control the delivery of fibrillation and defibrillation therapies, to generate current pulses to cause fibrillation, or to estimating the effectiveness of defibrillation therapy by, for example, computing a scaling exponent.

The invention may have one or more advantages. A single device may be used to deliver monophasic defibrillation therapy, multiphasic defibrillation therapy and fibrillation therapy. The device processor may use much of the same circuitry to deliver each type of therapy, thereby saving of space, weight and expense. An operator arriving on the scene of an emergency may be able to deliver fibrillation and defibrillation therapies to patients exhibiting asystole or PEA. The operator may also be able to provide monophasic or multiphasic defibrillation therapy.

Many kinds of defibrillators may practice the techniques of the invention, even though different kinds of defibrillators may respond to different degrees of operator control. A manual defibrillator, for example, may practice the techniques of the invention by applying fibrillation and defibrillation therapies under the control of an operator. An AED, by contrast, may apply the therapies automatically.

Moreover, the techniques of invention may be practiced by devices other than conventional defibrillators. For example, the techniques of invention may be practiced by a chest compressor that includes defibrillation capability, or other medical device that can perform defibrillation or control a defibrillator.

Fibrillation therapy may be used rarely. For a patient exhibiting asystole or PEA, however, fibrillation therapy followed by defibrillation therapy may represent the best chance for saving the life of the patient. For some patients, these therapies may make the difference between life and death.

In addition, some embodiments of the invention include techniques for controlling the timing of fibrillation and defibrillation therapies, that may further enhance the chance of survival of the patient. By monitoring the scaling exponent, for example, the defibrillator may deliver defibrillation therapy at a time that will benefit the patient.

The preceding specific embodiments are illustrative of the practice of the invention. Various modifications may be made without departing from the scope of the claims. For example, the interface and fibrillation circuit need not be combined as depicted in FIG. 1, but may be distinct components.

A defibrillator may implement a waiting period of a predetermined duration, rather than using the scaling exponent as an indicator of a good opportunity to attempt defibrillation therapy. In addition, a defibrillator may use indicators in place of or in addition to the scaling exponent. For example, the defibrillator may evaluate morphological characteristics of the ventricular fibrillation waveform other than fractal self-similarity dimension. These and other embodiments are within the scope of the following claims.

The invention claimed is:

1. A device comprising:
   a monitoring module to monitor electrical activity of a heart of a patient;
   an electrical source capable of generating a first electrical shock and a second electrical shock;
   at least two electrodes to deliver the first and second shocks to the heart; and
   a processor configured to determine that the heart is in asystole and, in response to the determination of asystole, control the electrical source to generate the first electrical shock in a manner intended to induce fibrillation,
   wherein the processor is further configured to control the electrical source to generate the second electrical shock in a manner intended to defibrillate the heart subsequent to the generation of the first electrical shock, and
   wherein the processor is further configured to compute, following delivery of the first electrical shock, a value representing an estimated effectiveness of the second electrical shock in defibrillating the heart prior to delivery of the second electrical shock, and
   wherein the processor is further configured to control delivery of the second electrical shock when a comparison between the value representing the estimated effectiveness of the second electrical shock and a predetermined value indicates that delivery of the second shock has an acceptable probability of defibrillating the heart.

2. The device of claim 1, wherein the monitoring module comprises an output device to display the electrical activity of the heart of the patient.

3. The device of claim 1, wherein the value representing the effectiveness of the second electrical shock comprises a scaling exponent that represents the likely outcome of defibrillation therapy.

4. The device of claim 1, further comprising an energy storage device to store energy for delivery for the first electrical shock and the second electrical shock.

5. The device of claim 4, further comprising a charging circuit to store energy in the energy storage device.

6. The device of claim 5, further comprising a battery to power the charging circuit.

7. The device of claim 5, further comprising an adapter to couple the device to an electrical outlet and power the charging circuit.

8. The device of claim 7, wherein the electrical source comprises a transformer to generate the first electrical shock by stepping down a voltage of current drawn via the electrical outlet.

9. The device of claim 1, further comprising an output device coupled to the processor and configured to be controlled by the processor to prompt an operator to perform cardiopulmonary resuscitation (CPR).

10. The device of claim 1, further comprising a chest compressor coupled to the processor and configured to be controlled by the processor to physically compress the chest of the patient.

11. The device of claim 1, further comprising an input device to receive a diagnosis from an operator, the input device being coupled to the processor for transmission of the diagnosis to the processor.

12. The device of claim 1, wherein the electrodes comprise external electrodes.

13. The device of claim 1, wherein the processor is configured to wait for a waiting period between controlling delivery of the first electrical shock and controlling delivery of the second electrical shock.

14. The device of claim 9, wherein the processor controls the output device to prompt the operator to perform CPR on the patient following delivery of the first electrical shock.

15. The device of claim 14, wherein the processor controls the output device to prompt the operator to discontinue performing CPR on the patient prior to delivery of the second electrical shock.

16. The device of claim 1, further comprising a chest compressor, wherein the processor controls the chest compressor to perform cardiopulmonary resuscitation (CPR) on the patient following delivery of the first electrical shock.

17. The device of claim 16, wherein the processor controls the chest compressor to discontinue performing CPR on the patient prior to delivery of the second electrical shock.

18. The device of claim 1, wherein the processor controls delivery of a defibrillation shock through the at least two electrodes to the heart when the heart is in fibrillation prior to delivery of the first and second electrical shocks, monitors electrical activity of the heart after delivery of the defibrillation shock, and controls delivery of the first electrical shock to induce fibrillation of the heart when asystole follows the defibrillation shock.

19. A device comprising:
    a monitoring module to monitor electrical activity of a heart of a patient, the monitoring module including a processor;
    an electrical source to generate a first electrical shock to induce fibrillation of the heart and a second electrical shock to defibrillate the heart; and
    at least two electrodes to deliver the first and second shocks to the heart,
    wherein the processor is configured to control the electrical source in a manner that instructs the electrical source to deliver the first electrical shock to induce fibrillation in response to the monitoring module detecting asystole and, subsequent to delivery of the first electrical shock, control the electrical source to deliver the second electrical shock, and
    wherein the processor is further configured to compute, following delivery of the first electrical shock, a value representing an estimated effectiveness of the second electrical shock in defibrillating the heart prior to delivery of the second electrical shock, and control the electrical source in a manner that instructs the electrical source to deliver the second electrical shock to defibrillate the heart when a comparison between the value representing the estimated effectiveness of the second electrical shock and a predetermined value indicates that delivery of the second shock has an acceptable probability of defibrillating the heart, and wherein the electrical source generates the first electrical shock to induce fibrillation by generating a fibrillation shock comprising a sequence of pulses, and modulating a width of at least one of the pulses.

20. The device of claim 19, wherein the electrical source modulates the width of the at least one of the pulses to cause the sequence to approximate a 60 Hz sine wave when the sequence is delivered to the heart.

21. The device of claim 19, wherein the electrical source modulates the width of the at least one of the pulses to cause the sequence to approximate a sine wave having a first amplitude, generates a second fibrillation shock comprising a second sequence of pulses, and modulates a width of at least one of the pulses in the second sequence to cause the second sequence to approximate a sine wave having a second amplitude.

22. The device of claim 19, wherein the electrical source modulates the width of the at least one of the pulses to cause the sequence to approximate a sine wave having a first frequency when the sequence is delivered to the heart, generates a second fibrillation shock comprising a second sequence of pulses, and modulates a width of at least one of the pulses in the second sequence to cause the second sequence to approximate a sine wave having a second frequency when the second sequence is delivered to the heart.

23. The device of claim 19, wherein the electrical source generates a fibrillation shock by generating a first sequence of pulses in one direction and a second sequence of pulses in the opposite direction.

24. A device comprising:
a monitoring module to monitor electrical activity of a heart of a patient;
an electrical source to generate a first electrical shock to induce fibrillation of the heart and a second electrical shock to defibrillate the heart;
at least two electrodes to deliver the first and second shocks to the heart; and
a processor configured to determine if the heart is in asystole and, if the heart is in asystole, control the electrical source so as to cause the electrical source to deliver a first electrical shock which is designed to induce fibrillation and subsequently deliver a second electrical shock which is designed to defibrillate the heart, and to estimate the effectiveness of the second electrical shock prior to its delivery by computation of a scaling component.

25. The device of claim 24, further comprising an output device coupled to the processor and configured to be controlled by the processor to prompt an operator to perform cardiopulmonary resuscitation (CPR).

26. The device of claim 24, further comprising a chest compressor coupled to the processor and configured to be controlled by the processor to physically compress the chest of the patient.

27. The device of claim 24, further comprising an input device to receive a diagnosis from an operator, the input device being coupled to the processor for transmission of the diagnosis to the processor.

28. The device of claim 24, wherein the electrodes comprise external electrodes.

29. The device of claim 24, wherein the processor is configured to wait for a waiting period between controlling delivery of the first electrical shock and controlling delivery of the second electrical shock.

30. A device comprising:
a circuit to convert direct current to alternating current;
a monitoring module to monitor electrical activity of a heart of a patient;
an electrical source capable of generating a first electrical shock and a second electrical shock;
at least two electrodes to deliver the first and second shocks to the heart; and
a processor configured to determine that the heart is in asystole and, in response to the determination of asystole, control the electrical source to generate the first electrical shock in a manner intended to induce fibrillation, and
wherein the processor is further configured to compute, following delivery of the first electrical shock, a value representing an estimated effectiveness of the second electrical shock in defibrillating the heart prior to delivery of the second electrical shock, and control the electrical source to generate the second electrical shock in a manner intended to defibrillate the heart subsequent to the generation of the first electrical shock when a comparison between the value representing the estimated effectiveness of the second electrical shock and a predetermined value indicates that delivery of the second shock has an acceptable probability of defibrillating the heart.

31. The device of claim 30, wherein the circuit is an H-bridge circuit.

32. The device of claim 31, wherein the H-bridge circuit comprises at least one switch to regulate the direction of current flow through the H-bridge circuit, and wherein the processor is further configured to control the switch.

33. The device of claim 30, wherein the electrical source generates the first electrical shock by generating an alternating current.

* * * * *

UNITED STATES PATENT AND TRADEMARK OFFICE
CERTIFICATE OF CORRECTION

PATENT NO.       : 8,036,742 B2                                           Page 1 of 1
APPLICATION NO.  : 10/357267
DATED            : October 11, 2011
INVENTOR(S)      : Joseph L. Sullivan, Fred W. Chapman and Robert G. Walker It is certified that error appears in the above-identified patent and that said Letters Patent is hereby corrected as shown below:

Column 7, line 45 should read "through patient Z1 in the direction indicated by arrow I2."
Column 7, line 48 should read "patient Z1 in the direction opposite that indicated by arrow I2."

Signed and Sealed this
Twenty-third Day of October, 2012

David J. Kappos
*Director of the United States Patent and Trademark Office*